(12) United States Patent
Deleo et al.

(10) Patent No.: US 7,906,514 B1
(45) Date of Patent: Mar. 15, 2011

(54) ANIMAL MODEL AND COMPOUNDS IDENTIFIED VIA THIS MODEL FOR TREATMENT OF CHRONIC PAIN

(75) Inventors: Joyce A. Deleo, Lebanon, NH (US); James N. Weinstein, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/857,385

(22) PCT Filed: Oct. 28, 1999

(86) PCT No.: PCT/US99/25187
§ 371 (c)(1),
(2), (4) Date: Jul. 6, 2001

(87) PCT Pub. No.: WO00/33830
PCT Pub. Date: Jun. 15, 2000

(51) Int. Cl.
*A61K 31/495* (2006.01)
*A61K 31/519* (2006.01)
*A61B 17/12* (2006.01)

(52) U.S. Cl. ...... 514/251; 514/256; 514/249; 514/262.1

(58) Field of Classification Search .................. 514/565, 514/251, 256, 262.1
See application file for complete search history.

(56) References Cited

U.S. PATENT DOCUMENTS 5,180,716 A * 1/1993 Yaksh et al. .................... 514/58

OTHER PUBLICATIONS

Geyer et al., Radiation, Methotrexate, and White Matter Necrosis: Laboratory Evidence of rNeural Radioprotection with Preirradiation Methotrexate. Int. J. Radiation Oncology, Biology, Physics, Aug. 1988, vol. 15, No. 2, pp. 373-375.*

Mori, M. et al. "General Pharmacological Studies of Methotrexate and 7-hydroxymethotrexate", Oyo Yakuri (1996) vol. 52, No. 6, pp. 459-470, see abstract.*
Chamberlain et al. *Carcinomatous meningitis* secondary to breast cancer: Predictors of response to combined modality therapy Oct. 1997, Journal of Neuro-Oncology 35(1) pp. 55-64.*
Leger et al. Lymphome-induced polyradiculopathy in AIDS: two cases, Mar. 1992, Journal of Neurology, vol. 239 No. 3 pp. 132 134.*
O'Neill et al. Treatable *lumbosacral polyrddiculitis* masquerading as diabetec amyotrophy, Oct. 22, 1997 Journal of the Neurological Sciences vol. 151, No. 2 pp. 223-225.*
Chamberlain et al., *Carcinoma meningitis* Secondary to Non-Small Cell Lung Cancer, Apr. 1998, Archives of Neurology, vol. 55, No. 4, pp. 506-512.*
Chamberlain et al. *Carcinoma meningitis* Secondary to Non-Small Cell Lung Cancer, Archives of Neurology; Apr 1998; 55, 4 pp. 506-512.*
Biomethodology of the Rat, http://research.uiowa.edu/animal/print.php?get=rat; print date Jun. 13, 2007.*
Heywood et al., Cervical Spine INstability in Rheumatoid Arthritis, The Journal of Bone and Joint Surgery, vol. 70-B No. 5 Nov. 1988, pp. 702-707.*
Drug Facts and Comparisons, 1994, Wolters Kluwer Co. pp. 1243-1244.*
Mori et al., "General Pharmacological Studies of Methotrexate and 7-hydroxymethotrexate", Oyo Yakuri 1996 52 (6) 459-470.
Geyer et al., "Radiation, Methotexate, and White Matter necrosis: Laboratory Evidence for Neural Radioprotection with Preirradiation Methotrexate", *Int. J. Radiation Oncology, Biology, Physics* 1988 15 (2) 373-375.
Goldenberg M.M., "Leflunomide, a Novel Immunomodulator for the Treatment of Rheumatoid Arthritis", *Clin. Ther.* 1999 21(11):1837-1852.

* cited by examiner

*Primary Examiner* — Yvonne L Eyler
*Assistant Examiner* — Donna Jagoe
(74) *Attorney, Agent, or Firm* — Licata & Tyrrell, P.C.

(57) ABSTRACT

An animal model for chronic pain, and in particular lower back pain, is provided. Methods of identifying agents and reducing chronic pain with identified agents such as methotrexate are also provided.

1 Claim, No Drawings

ANIMAL MODEL AND COMPOUNDS IDENTIFIED VIA THIS MODEL FOR TREATMENT OF CHRONIC PAIN

This research was funded in part by a grant from the National Institute of Arthritis and Musculoskeletal and Skin Diseases (Grant No. AR44757). The U.S. government may therefore have certain rights in this invention.

BACKGROUND

Chronic pain associated with the lower back is a common problem that will affect approximately two thirds of the adult population at some point in their lives (Deyo et al. 1987. *Spine* 12:264-268). It is the second leading reason for ambulatory care in the United States and direct medical costs are estimated at over $20 million per year (Frymoyer et al. 1991. *Orthop. Clin. North Am.* 22:263-271). A small but significant percentage of patients suffering from lower back pain exhibit symptoms of radicular pain associated with a herniated disk (i.e., persistent lumbar radiculopathy). Current treatment for persistent lumbar radiculopathy includes, but is not limited to, invasive surgical procedures, pharmacological therapy, and physical therapy.

Two mechanisms for production of radicular pain with or without herniated intervertebral discs have been proposed (McCarron et al. 1987. *Spine* 12:760-764; Olmarker, et al. 1989. *J. Orthop. Res.* 7:817-823; Olmarker et al. 1993. *Spine* 18:1425-1432; Kawakami et al. 1994. *Spine* 19:1780-1794). The first mechanism involves mechanical compression of the spinal root, while the second involves a biological inflammatory effect on the root induced by the herniated nucleus pulposus. However, the absence of animal models for lower back pain associated with radiculopathy has hindered the understanding of the pathophysiological mechanisms that produce radicular pain. Thus, the exact contribution of each component and elucidation of the specific role of each has not been established.

The majority of pain research using animal models has focused on injury to a peripheral nerve, in most cases the sciatic nerve. These peripheral nerve injury models in the rat reliably result in behaviors suggestive of neuropathic pain in humans (Wall et al. 1979. *Pain* 7:103-111; Bennett and Xie. 1988. *Pain* 33:87-107; Seltzer et al. 1990. *Pain* 43:205-218; DeLeo et al. 1991. *Cryobiology.* 28:460-466; DeLeo et al. 1994. *Pain* 56:9-16; Kim and Chung. 1992. 43:428-437). However, root lesions central to the dorsal root ganglion lead to a sequence of events that differs from lesions of peripheral nerves. Therefore, it is not possible to simply extrapolate from information gained from peripheral nerve injury in animal models and apply the findings to an understanding of the etiology of lumber radiculopathy. Therefore, animal models of lumbar radiculopathy are essential to the understanding of the etiology of lower back pain and the pathophysiology of radiculopathy.

It has been suggested that central, neuroimmune mechanisms are an important factor in the development and maintenance of chronic neuropathic pain, such as persistent lumbar radiculopathy (DeLeo et al. 1996. *J. Interferon Cytokine Res.* 16:695-700; DeLeo et al. 1997. *Eur. J. Pain* 1:115-122). Many of the events that induce hyperalgesia activate immune cells, both centrally and peripherally. Enhanced spinal neuroimmune responses have been reported in models of neuropathy, responses such as glial activation and increases in proinflammatory cytokines (Colburn et al. 1997. *J. Neuroimmunol.* 79:163-175; DeLeo et al. 1996. *Cytokine res.* 16:695-700; DeLeo et al. 1997. *Brain Res.* 759:5-57).

Methotrexate is a folate antagonist originally developed for treatment of malignancies and now widely used in the treatment of rheumatoid arthritis due to its potent, selective, immunosuppressive actions. Methotrexate has also been used in the treatment of psoriasis, a non-neoplastic disease of the skin characterized by rapid proliferation of epidermal cells, as well as in allogenic bone marrow and organ transplantation, treatment of dermatomyositis, Wegener's granulomatosis, and Crohn's disease (Chabner et al. 1996. In: *Goodman & Gilman's The Pharmacological Basis of Therapeutics*, Chapter 51). As a result, the clinical safety profile of this drug has been well-established.

A new animal model for chronic pain has now been developed. Using this new model, it has now been found that methotrexate is an effective agent for the treatment of lower back pain with or without disc herniation and may be useful in the treatment of chronic neuropathic and radicular pain.

SUMMARY OF THE INVENTION

An object of the present invention is to provide a method of preventing and reducing pain in an animal, and in particular lower back pain, which comprises administering to the animal methotrexate.

Another object of the present invention is a non-human animal model for radicular pain wherein the L5 spinal root of the animal is loosely ligated with a suture material, preferably chromic gut.

Another object of the present invention is to provide a method for producing a nonhuman animal model for radicular pain which comprises: anesthetizing a nonhuman animal with inhalation anesthesia; making an incision in the skin and muscle layers at a L5 level of the spinal cord of the nonhuman animal; exposing the spinal root, the dorsal root ganglia, and the adjacent dura mater on the left side at the L5 level of the spinal cord of the nonhuman animal; securing pieces of suture material, preferably chromic gut, around the spinal root adjacent to the L5 position; and suturing the muscle layers and the skin incisions of the animal closed.

Yet another object of the present invention is to provide a method of evaluating efficacy of an agent for use in chronic pain management comprising administering a test agent to this nonhuman animal model and determining the ability of the test agent to inhibit or prevent mechanical allodynia or gait disturbance in the animal.

DETAILED DESCRIPTION OF THE INVENTION

Treatment of chronic pain involves use of a variety of analgesic agents, with the goal of therapy being reduction of pain symptoms with the least amount of side effects. Many of the commonly used analgesics produce marked central nervous system depression and impair the ability of the patient to perform even daily routine activities. It has now been found that methotrexate, a drug used for treatment of cancer as well as a variety of other conditions associated with rapid cell growth, is a novel and effective treatment for chronic pain, and in particular lower back or radicular pain.

A spinal root injury animal model has now been developed in the rat to aid in research into chronic pain and new treatment regimens for such pain. In this animal model, the L5 spinal root of a nonhuman animal is loosely ligated with a suture material such as chromic gut or silk suture. This model, which is a modification of the Bennett chronic constriction injury model of the sciatic nerve (Bennett, G. J. and Y. K. Xie. 1988. *Pain* 33:87-107) produces thermal hypersensitivity and mechanical allodynia by day one following surgery which resolves within 3-4 weeks. Allodynia is the sensation of pain produced by a normally non-painful stimulus. Animals of this model exhibit a graded, mechanical allodynia dependent on the type of root injury, i.e., ligation with inflammatory chromic gut, tight ligation with silk suture, or loose ligation with silk suture. Radiculopathic symptoms resolve within 10 days when the root is loosely ligated with hypoxic silk suture. Accordingly, to predict robust pain behaviors in this model, it is preferred that the ligation be made with chromic gut as ligature with this material not only mechanically compresses the spinal root but also chemically stimulates an inflammatory response. Thus, by ligating the spinal root with chromic gut, this animal injury model is useful for study of the pathophysiologic mechanisms of radicular pain since the chromic gut models both the inflammatory component of herniated nucleus pulposus and the ligation models root compression.

This nonhuman animal model is useful in evaluating the efficacy of agents in treating chronic pain, and in particular lower back pain, in humans. Agents suspected of being useful in chronic pain management can be administered to an animal of this model. The ability of this agent to prevent mechanical allodynia or reduce existing mechanical allodynia in these animals can then be evaluated. The ability of these agent to prevent gait disturbance in these animals can also be evaluated. Agents which prevent or inhibit mechanical allodynic or gait disturbance in these animals should be useful in chronic pain management in humans.

For example, using this new animal model for chronic pain, a two phase study was designed to examine the effects of methotrexate on both the prevention of mechanical allodynia as well as the efficacy of methotrexate for reducing existing mechanical allodynia following lumbar root injury.

The first phase of the study investigated three combinations of treatments: 1) Group A—methotrexate administration locally (intrathecally) to the surgical area immediately following surgery, followed by additional methotrexate administration locally at days 2 and 4 post-surgery; 2) Group B—saline administration locally to the surgical area immediately following surgery and at days 2 and 4 post-surgery; and 3) Group C—sham-operated animals that received methotrexate at the same time points. In all animals, gait disturbance and mechanical allodynia were assessed until animals were euthanized 7 days after surgery.

In the second phase of the study, animals were assessed out to day 14 post-surgery and given additional treatments as follows: 1) Group D—surgically prepared, saline treated rats were then given methotrexate locally during the second week of the study on days 7, 9, and 11 post-surgery; 2) Group E—surgically prepared, saline treated rats were then given saline locally during the second week on days 7, 9, and 11 post-surgery; and 3) Group F—surgically prepared, methotrexate treated rats were then given saline during the second week on days 7, 9, and 11 post-surgery. Gait disturbance and mechanical allodynia were assessed before surgery and at days 2, 4, 7, 9, 11, and 14 until euthanization.

All rats in Groups A and B demonstrated inversion of the ipsilateral hind paw. Forty percent of rats in these groups also showed a slight gait disturbance that gradually improved until normal gait was restored by day 7 post-surgery. There was no significant difference in the postoperative changes in hind paw inversion or gait disturbance between Groups A and B. The sham-operated animals in Group C did not demonstrate any hind paw inversion or gait disturbance, therefore there were significant differences in their postoperative changes as compared to Groups A and B.

Behavioral responses after surgery were compared to baseline measurements of allodynia. The rats rarely demonstrated baseline stimulation responses before the surgery. However, rats in Group B demonstrated mechanical allodynia from one day post-surgery to the time of euthanization at day 7. Allodynia was significantly reduced in Group A (injury+methotrexate) toward the baseline after the peak response at day 2 post-surgery. Rats in Group C (sham-operated+methotrexate) demonstrated only a minimal response after surgery. Therefore, methotrexate was capable of reducing and preventing, mechanical allodynia in this animal model of lower back pain.

During phase II of the study, rats in all three groups demonstrated a similar time course in gait disturbance regardless of their post-operative treatments. All animals had a normal gait at the time of euthanization at day 14. Rats in Groups D and E (saline-treated animals) showed a robust allodynic response which developed by day 2 post-surgery and continued up to day 7 post-surgery. There was no difference in response scores for mechanical allodynia in Groups D and E at day 7. However, during the second week, mechanical allodynia significantly decreased in the methotrexate-treated Group D, while mechanical allodynia continued to persist in the saline-treated Group E. Animals in Group F which were treated with methotrexate after the first week post-surgery only (during week two only) demonstrated allodynia which gradually decreased after the peak at day 2 post-surgery. At day 7 post-surgery, allodynia was significantly attenuated in Group F as compared to Groups D and E. During the second week when treatment was with methotrexate rather than saline, the allodynic response remained significantly lower as compared to Group E.

Gross pathological inspection following euthanasia revealed no evidence of suppurative inflammation around the nerve roots or dorsal root ganglia in any of the animals. In all groups except the sham-operated animals (Group C), the treated nerve roots were encapsulated with dense granulation tissue and fibrous adhesions. Granulation and adhesion around the injured nerve roots were markedly decreased in the methotrexate-treated groups (A, D and F) as compared to saline-treated groups (B and E).

Immunohistochemical analysis of glial cells revealed that markers for activation of glial cells, OX-42 and GFAP (glial fibrillary acidic protein), were elevated in all groups that underwent root ligature with chromic gut (Groups A, B, D, E and F). There was a significant difference in the level of glial activation between the methotrexate-treated groups and the saline-treated groups.

These data demonstrate that methotrexate significantly attenuates mechanical allodynia in a lower back pain model with radiculopathy following local administration. The observation that granulation and adhesion around the injured nerve root was less in the methotrexate-treated groups demonstrates that methotrexate reduces inflammation around the nerve root that had been caused by chromic gut-induced inflammation. Therefore, methotrexate demonstrated activity as an anti-inflammatory agent or immunomodulator in the spinal cord and/or at the injury site.

The dosage of methotrexate shown to be effective in these studies was low, 1 mg/kg. Clinical experience with methotrexate is widespread, with doses used dependent on the desired clinical effect, and doses ranging as high as 250 mg/kg when used as a chemotherapeutic agent and as low as 0.1 mg/kg when used to treat rheumatoid arthritis. One of skill would choose a dose to be administered to an animal, including a human, based on the ranges reported in the literature to be without adverse effects. The methotrexate dose administered to rats in the present invention, 1 mg/kg, was one quarter of the maximally tolerated dose for rats (a dose without acute neurotoxic effects; Morris et al. 1992. *Br. J. Radiol.* 65:152-156). Methotrexate can be administered orally, intravenously, intramuscularly or intrathecally, however, it diffuses poorly into cerebrospinal fluid. Therefore, one of skill would be able to choose an appropriate route of administration and dose based on the known toxicity of this drug. The doses shown to be effective in the rat are well below the toxicity levels for methotrexate (Chabner et al. 1996. In: *Goodman & Gilman's The Pharmacological Basis of Therapeutics*, Chapter 51). Further, this drug may be administered to an animal, including a human, with any type of neuropathic pain, as the animal model tested is one which is useful for examining neuropathic pain in general.

The following non-limiting examples are presented to further illustrate the present invention:

EXAMPLES

Example 1

Surgery for Production of Rat Model for Lower Back Pain

Male Holtzman rats (200-250 g) were used. All surgical procedures were performed under inhalation anesthesia (induced at 4% and maintained at 2% halothane in 100% $O_2$). Spinal root, dorsal root ganglia, and the adjacent dura mater on the left side at L5 were carefully exposed by hemilaminectomy using a surgical microscope. Five 0.3 cm pieces of 4-0 chromic gut ligature were laid adjacent to the root and secured by two loose ligatures of 5-0 chromic gut. The muscle layers and incision were closed with 3-0 silk suture and staples, respectively.

For phase I, three combinations of treatments were investigated. Methotrexate was reconstituted to 10 mg/ml in saline and pH adjusted to 7.4. Group A represented root injury plus methotrexate treatment. Immediately following surgery and prior to incision closure, Group A rats received 1 mg/kg of methotrexate (volume 100 ul/kg) by injecting through a PE-10 catheter through an incision in the exposed dura mater to a position 3 cm central to the incision. The PE-10 catheter was pulled out and the same dose and volume of methotrexate (1 mg/kg) was administered around the injured nerve roots (total dose 2 mg/kg). The wound was closed. On days 2 and 4 post-surgery, under inhalation anesthesia, methotrexate was again administered by opening the surgical wound and repeating delivery of methotrexate as before.

Group B animals represented root injury plus saline treatment. Saline was administered intrathecally and perineurally in the same manner as in Group A above at the time of surgery (200 ul/kg volume) and at days 2 and 4 post-surgery.

Group C animals represented sham-operated plus methotrexate treatment. In these animals, the L5 nerve roots were exposed but not injured. Methotrexate was administered using the same dose, protocol, and time points as Group A.

In all animals, gait disturbance and mechanical allodynia were assessed until euthanization at day 7 post-surgery.

For phase II of the study, the protocol was extended to day 14 with the surgery, delivery method, volume and doses being identical to those of the phase I study. Rats were divided into 3 groups. Group D represented saline plus methotrexate treatment. Saline was administered at the time of surgery and at days 2 and 4 post-surgery. Methotrexate was administered in the second week at days 7, 9 and 11 post-surgery.

Group E represented saline plus saline treatment. In these rats, saline was administered throughout the two weeks at the same time points as in Group D.

Group F represented methotrexate plus saline treatment. In these rats, methotrexate was administered during surgery and at days 2 and 4 post-surgery. Saline was then administered on days 7, 9, and 11 post-surgery. Gait disturbance and mechanical allodynia were also assessed in these animals at days 2, 4, 7, 9, 11 and 14 (day of euthanization).

Example 2

Gait Disturbance and Hind Paw Inversion Testing

Animals were tested for 3 days pre-operatively to acclimate to the testing apparatus and the experimenter, and to obtain baseline values. All testing was performed by experimenters blinded to the treatments. Gait disturbance was scored using a rating scale. Normal gait was rated as (−), slight gait disturbance with motor weakness was rated as (+), while severe gait disturbance with motor paresis of the ipsilateral hind paw was rated as (++). The presence or absence of hind paw inversion described as plantar flexion of the toes and/or the presence of an inverted hind paw (the toes were held together or retroflexed on the hind paw) was also recorded.

Example 3

Mechanical Sensitivity (Allodynia) Testing

Animals were tested for 3 days pre-operatively to acclimate to the testing apparatus and the experimenter, and to obtain baseline values. All testing was performed by experimenters blinded to the treatments. Tactile sensitivity (mechanical allodynia) was measured as the frequency of foot withdrawals elicited by a defined mechanical stimulus (DeLeo et al. 1996. *J. Interferon Cytokine Res.* 16:695-700; Colburn, et al. 1997. *J. Neuroimmunol.* 79:163-175). In each blinded testing session, rats were subjected to 3 sequential series of 10 tactile stimulations to the plantar surface of the ipsilateral (nerve root injured) hind paw using 2 g and 12 g von Frey filaments (Stoelting, Wood Dale, Ill.). Baseline (pre-lesion) responsiveness was minimal as confirmed from testing sessions prior to surgery. Mechanical allodynia was assessed by recording the total number of responses elicited during three successive trials (10 stimulations/filament) separated by at least 10 minutes for a total possible score of 30. The terms for the allodynic condition were defined as follows: minimal (0-5), mild (5-10), moderate (10-15, and robust (15 or more).

Example 4

Immunohistochemical Analysis

All animals were perfusion fixed for immunohistochemistry. Under deep anesthesia (sodium pentobarbital, 50 mg/kg intraperitoneally) rats were euthanized by transcardiac perfusion. Rats were then perfused with 300 ml phosphate buffered saline (PBS) followed by 500 ml 4% paraformaldehyde in 0.1 M PBS. Following perfusion and laminectomy, the lesioned L5 roots were verified and traced to their site of entry into the spinal cord. Appropriate L5 spinal cord segments were harvested and post fixed for 4 hours in fixative and then cryoprotected 2-3 days in 30% sucrose/PBS at 4° C. The segments were then freeze-mounted in OCT embedding medium on cork blocks for cryostat sectioning.

Optimal dilutions and incubation time periods for each antibody and lot were determined prior to the study. Immunohistochemistry was performed with the avidin-biotin technique on free-floating 20 μm sections. Elimination of the primary antibody was performed in each run as a negative control. Monoclonal antibody OX-42 (labeling the complement receptor-3, CD11b) was used as a microglial marker at a dilution of 1:2. A rabbit polyclonal antibody to glial fibrillary protein (anti-GFAP, DAKO, Carpintra, Calif.) was used as an astrocytic marker at a dilution of 1:20,000. Five or more sections per animal were prepared from the L5 segments in each run.

Assessment of spinal microglial and astrocytic responses was performed by blinded experimenters. Following staining of lumbar spinal cord sections with the specific glial marker under consideration, all the sections from each animal were surveyed under low (10×) and medium (40×) magnification to arrive at a score based on a previously described scale (Colburn et al. 1997. *J. Neuroimmunol.* 79:163-175). The final score was based on the average reactivity of all sections per animal.

What is claimed is:

1. A method of reducing lower back pain with radiculopathy in an animal having lower back pain with radiculopathy consisting of locally administering methotrexate intrathecally into the spinal cord but not the brain of said animal at a dose level of 1 mg/kg every other day for up to 4 days, so that lower back pain with radiculopathy is reduced.

* * * * *